(12) United States Patent
Potyrailo et al.

(10) Patent No.: US 9,052,263 B2
(45) Date of Patent: Jun. 9, 2015

(54) METHODS FOR ANALYTE DETECTION

(75) Inventors: Radislav Alexandrovich Potyrailo, Niskayuna, NY (US); Matthew Damian Pietrzykowski, Clifton Park, NY (US); Yongjae Lee, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 469 days.

(21) Appl. No.: 13/484,674

(22) Filed: May 31, 2012

(65) Prior Publication Data

US 2012/0235690 A1    Sep. 20, 2012

Related U.S. Application Data

(63) Continuation-in-part of application No. 12/424,016, filed on Apr. 15, 2009, now Pat. No. 8,364,419.

(51) Int. Cl.
G01R 27/28 (2006.01)
G01N 27/02 (2006.01)

(52) U.S. Cl.
CPC ............ *G01N 27/028* (2013.01); *G01N 27/026* (2013.01)

(58) Field of Classification Search
CPC ........................... G01N 27/028; G01N 27/026
USPC ................... 702/19, 23, 24; 324/652
See application file for complete search history.

(56) References Cited

U.S. PATENT DOCUMENTS

| | | | | |
|---|---|---|---|---|
| 4,275,364 A * | 6/1981 | Skatvold, Jr. | | 333/33 |
| 5,744,902 A * | 4/1998 | Vig | | 310/360 |
| 6,360,585 B1 * | 3/2002 | Potyrailo et al. | | 73/24.06 |
| 6,406,668 B1 * | 6/2002 | Dordick et al. | | 422/82.07 |
| 6,818,450 B2 * | 11/2004 | Eaton et al. | | 436/52 |
| 8,364,419 B2 * | 1/2013 | Potyrailo et al. | | 702/24 |
| 8,452,716 B2 * | 5/2013 | Howley et al. | | 706/12 |
| 8,542,023 B2 * | 9/2013 | Potyrailo et al. | | 324/652 |
| 2002/0197725 A1 * | 12/2002 | Eaton et al. | | 436/104 |
| 2003/0154031 A1 * | 8/2003 | Potyrailo et al. | | 702/19 |
| 2007/0090926 A1 * | 4/2007 | Potyrailo et al. | | 340/10.41 |
| 2009/0215646 A1 * | 8/2009 | Anslyn et al. | | 506/12 |
| 2010/0153323 A1 * | 6/2010 | Hennessy et al. | | 706/20 |
| 2010/0268479 A1 * | 10/2010 | Potyrailo et al. | | 702/23 |
| 2011/0018649 A1 * | 1/2011 | David et al. | | 331/158 |
| 2012/0116683 A1 * | 5/2012 | Potyrailo et al. | | 702/19 |
| 2014/0025313 A1 * | 1/2014 | Potyrailo et al. | | 702/23 |

FOREIGN PATENT DOCUMENTS

EP       1967846 A1 *  9/2008

* cited by examiner

*Primary Examiner* — Carol S Tsai
(74) *Attorney, Agent, or Firm* — Eileen B. Gallagher

(57) ABSTRACT

A method is provided for selectively detecting the presence and concentration of at least four analytes in a mixture. In certain embodiments, the method comprises contacting a single sensor with the mixture of analytes, wherein the sensor comprises at least one resonant sensor circuit comprising a sensing material that comprises at least two material properties that change in the presence of four or more analytes in their mixtures, and generating a multivariate sensor response pattern. The methods disclosed herein further optionally comprise performing analyte classification and analyte quantitation. Methods for selectively detecting the concentration of at least one analyte in a mixture further comprising at least one interference are also described in the instant application.

2 Claims, 15 Drawing Sheets

METHODS FOR ANALYTE DETECTION

CROSS REFERENCE TO RELATED APPLICATIONS

This application is a continuation-in-part of U.S. application Ser. No. 12/424,016, filed on Apr. 15, 2009, which is herein incorporated by reference in its entirety.

BACKGROUND

The invention relates to sensors and methods for analyte detection, and more particularly to sensors and methods for chemical and biological sensing applications.

An appropriate selection of sensing material is one of the aspects in sensor performance and application. The key performance indicators for sensors are selectivity, sensitivity and reliability.

Selectivity is the ability of the sensor to respond only to a specific analyte or a group of analytes. High sensor selectivity is required to detect trace concentrations of analytes in the presence of other contaminants, which result in high background levels of interference. Currently known sensors do not exhibit high selectivity under such conditions.

Sensitivity of a sensor is the output produced per unit change in concentration of an analyte. Stability of the sensor sensitivity and selectivity are also important factors. This stability of sensitivity and selectivity of the sensor is known as reliability.

Impedance spectroscopy is a standard technique currently used to characterize fundamental aspects of material performance. In impedance spectroscopy, a sensing material is positioned between electrodes and is probed over a wide frequency range (from a fraction of Hz to tens of MHz) to extract the fundamental information about dielectric properties of the material and vapor effects on these properties. But applicability of impedance spectroscopy in practical sensors for detection of trace levels of analytes is limited due to its low sensitivity in reported measurement configurations and prohibitively long acquisition times over the broad frequency range.

Therefore, there is a need for sensing materials in combination with a proper transducer to achieve high levels of sensitivity, selectivity and reliability for identifying analytes.

BRIEF DESCRIPTION

In one embodiment, a system for selectively determining at least two analytes, comprising at least one resonant sensor circuit comprising a sensing material that predictably affects the resonant complex impedance response of a sensor electrode, wherein the sensing material comprises at least two material properties that change upon exposure to two or more analytes and a processor that generates a multivariate sensor response pattern that is based at least in part on a change in the two material properties of the sensing material.

In another embodiment, a system for selectively determining at least two analytes, comprising at least one resonant sensor circuit comprising a sensing material that predictably affects the resonant complex impedance response of a sensor electrode structure wherein the sensor electrode structure comprises an inductor-capacitor-resistor circuit and wherein the sensing material comprises at least two material properties that change upon exposure to two or more analytes and a processor that generates a multivariate sensor response pattern that is based at least in part on a change in the two material properties of the sensing material.

In yet another embodiment, a sensing device adapted to detect at least two analytes, comprising a resonant sensor circuit comprising a sensor electrode and a sensing material disposed on the sensor electrode, wherein the sensing material comprises at least two material properties that change upon exposure to two or more analytes; a processor that generates a multivariate sensor response pattern that is based at least in part on a change in the two material properties of the sensing material and a memory chip storing user-defined digital data.

In one embodiment, a method for selectively detecting at least two or more analytes in presence of an interference, comprising contacting a sensor with an analyte; wherein the sensor comprises at least one resonant sensor circuit comprising a sensing material comprises at least two material properties that change in the presence of two analytes; and generating a multivariate sensor response pattern.

In another embodiment, a method for selectively detecting concentrations of at least four analytes in their mixtures with a single sensor, comprising contacting a sensor with a mixture of analytes; wherein the sensor comprises at least one resonant sensor circuit comprising a sensing material that comprises at least two material properties that change in the presence of four or more analytes in their mixtures; and generating a multivariate sensor response pattern.

In an additional embodiment, a method for selectively detecting concentrations of at least four analytes in their mixtures with a single sensor, the method comprising contacting a sensor with a mixture of analytes; wherein the sensor comprises at least one resonant sensor circuit comprising a sensing material comprises at least two material properties that change in the presence of four or more analytes in their mixtures; generating a multivariate sensor response pattern; performing analyte classification; and performing analyte quantitation.

In a further aspect of this application, a method for selectively detecting concentrations of at least one analyte in a mixture that further comprises at least one unknown interference, the method comprising contacting a sensor with a mixture of at least one analyte and at least one unknown interference; wherein the sensor comprises at least one resonant sensor circuit comprising a sensing material that comprises at least two material properties that change in the presence of at least one analyte in the mixture that also comprises at least one unknown interference; and generating a multivariate sensor response pattern.

In another embodiment, a method for selective detection of at least two analytes with one wireless multivariate battery-free sensor system is described. The method comprises the steps of contacting at least two analytes with a sensor circuit, wherein the sensor circuit comprises at least one integrated circuit chip that is configured to accept inputs from at least two sensors, wherein the sensors are positioned in the proximity to the chip or are the integral part of the chip; detecting more than one analyte using at least two inputs into an integrated circuit chip of the sensor circuit where the inputs into the integrated circuit chip are from the same or from different sensing materials; determining a multivariate response pattern of the sensor system upon sensor exposure to different analytes, by performing a multivariate analysis of the response of at least two sensors; and identifying the analytes and concentrations of at least two analytes from this pattern, where one of analytes may be the analyte of interest to the end-user while the second analyte may be not of interest to the end-user (an interferent) or may be another analyte also of interest to the end-user.

Detected species include those in a gas phase, such as gases, vapors, and air-borne particles (e.g., mold, spores, pollen and any other known air-borne particles). Detected species also include those in a liquid phase, including but not limited to ions, non-ions in water, or biological species in water. Non-limiting examples of biological species include nucleic acids, proteins, spores, peptides, viruses, bacteria, and toxins.

DRAWINGS

These and other features, aspects, and advantages of the present invention will become better understood when the following detailed description is read with reference to the accompanying drawings in which like characters represent like parts throughout the drawings, wherein.

Figure 11:
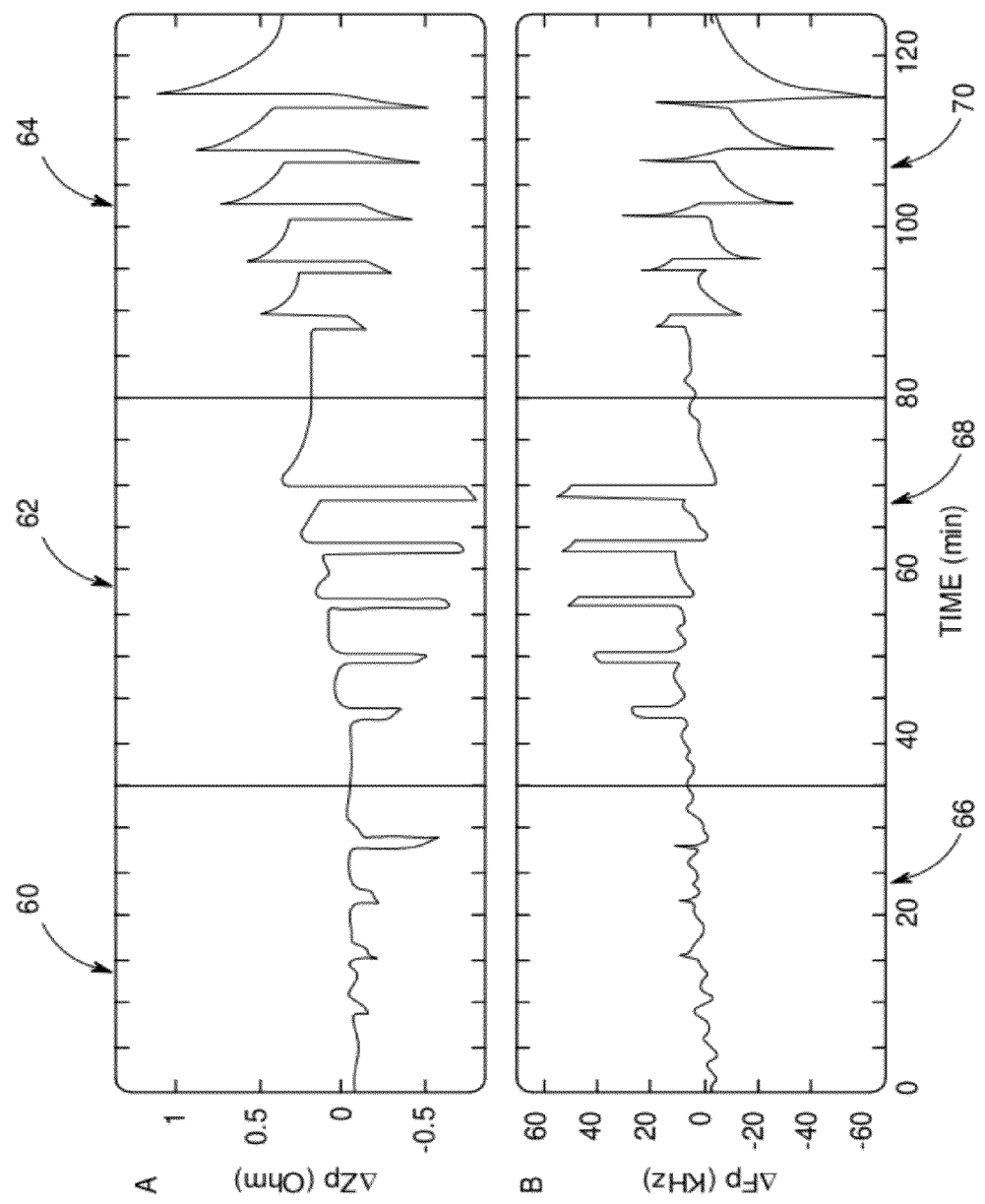

FIG. 11 provides graphs illustrating the selectivity of a sensor response to changes in the complex impedance $\Delta Zp$ (A) and frequency $\Delta Fp$ (B) for samples of water (60 and 66 respectively), trichloromethane (62 and 68 respectively) and dichloromethane vapors (64 and 70 respectively), wherein the sensor material comprises a homopolymer of triarylamines.

Figure 12:
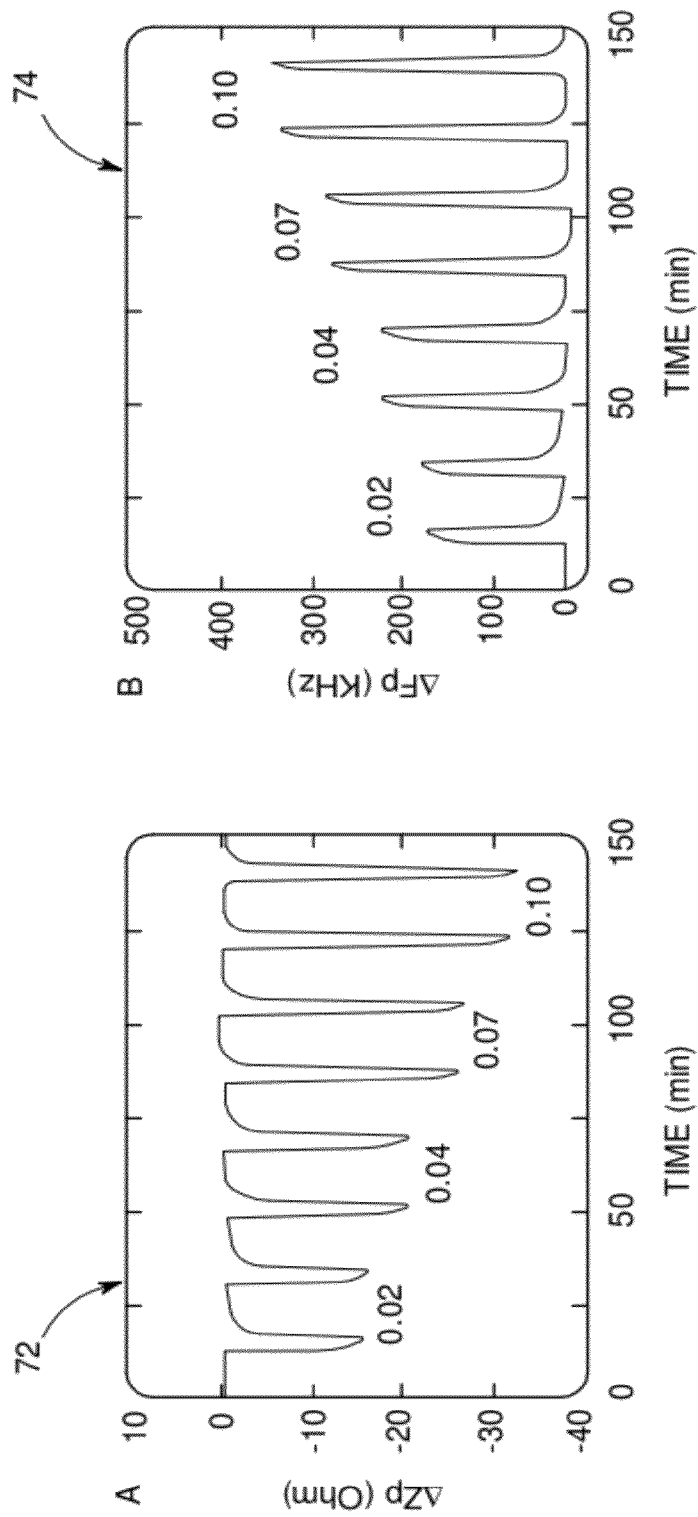

FIG. 12 is a graph illustrating the sensitivity of a sensor response to change in complex impedance $\Delta Zp$ (A) (72) and frequency $\Delta Fp$ (B) (74) for a sample of toluene vapor, wherein the sensing material comprises a copolymer of 80% fluorenes and 20% triarylamines.

Figure 13:
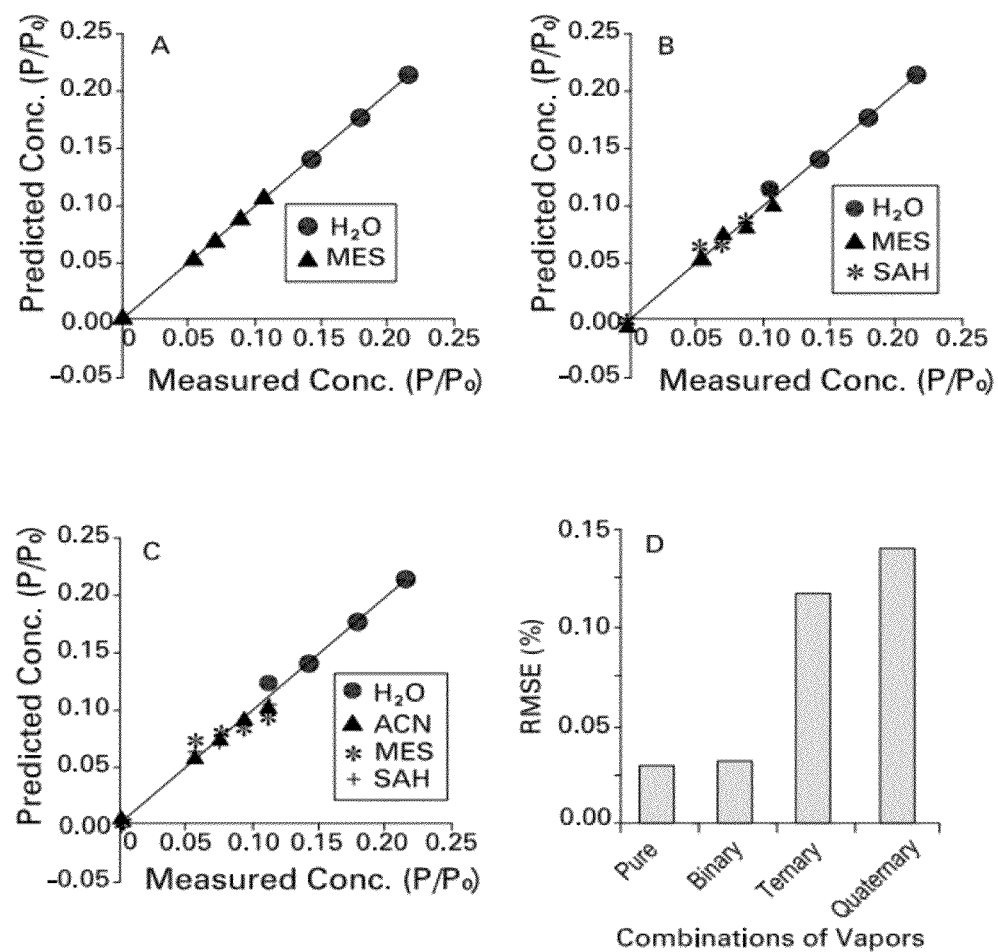

FIG. 13 is a graph illustrating the quantitation of a sensor response of individual vapors: water (H2O), acetonitrile (ACN), methyl salicylate (MeS), and salicylaldehyde (SAH) as binary, ternary, and quaternary mixtures. (A) provides the results with a binary mixture of $H_2O$ and MeS; (B) provides the results of a ternary mixture of $H_2O$, MeS, and SAH; and (C) provides the results of a quaternary mixture of $H_2O$, ACN, MeS, and SAH. (D) provides the Statistics of Root Mean Square Error (RMSE) of calibration for pure, binary, ternary, and quaternary mixtures.

Figure 14:
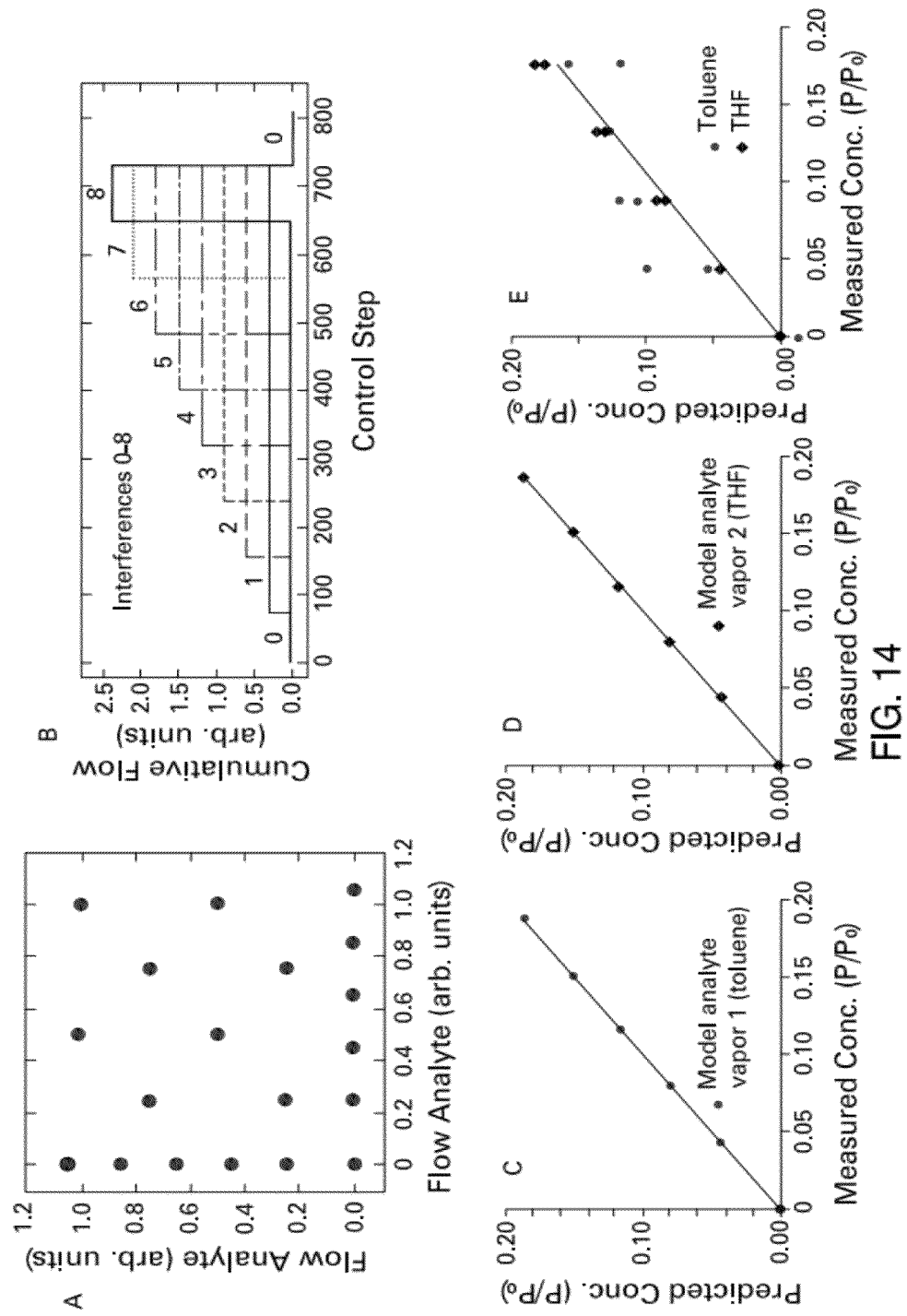

FIG. 14 is a graph illustrating the quantitation of a two-vapor response pattern in the presence of up to eight interference vapors. (A) provides the pattern of concentrations of two model analyte vapors with their individual concentrations and mixtures; (B) provides the steps of carrier gas (0) and interference vapors (1-8). Analyte vapors were added at each step, as shown in C and D. Correlation plots predicting concentrations of individual vapors (see E and F) and their binary mixture (See G) in the presence of eight interference vapors. Analyte vapors were (1) toluene and (2) tetrahydrofuran (THF). Interference vapors (1-8) included water, acetonitrile, acetone, methyl salicylate, ethanol, 1-pentanol, 1-propanol, and salicylaldehyde.

Figure 15:
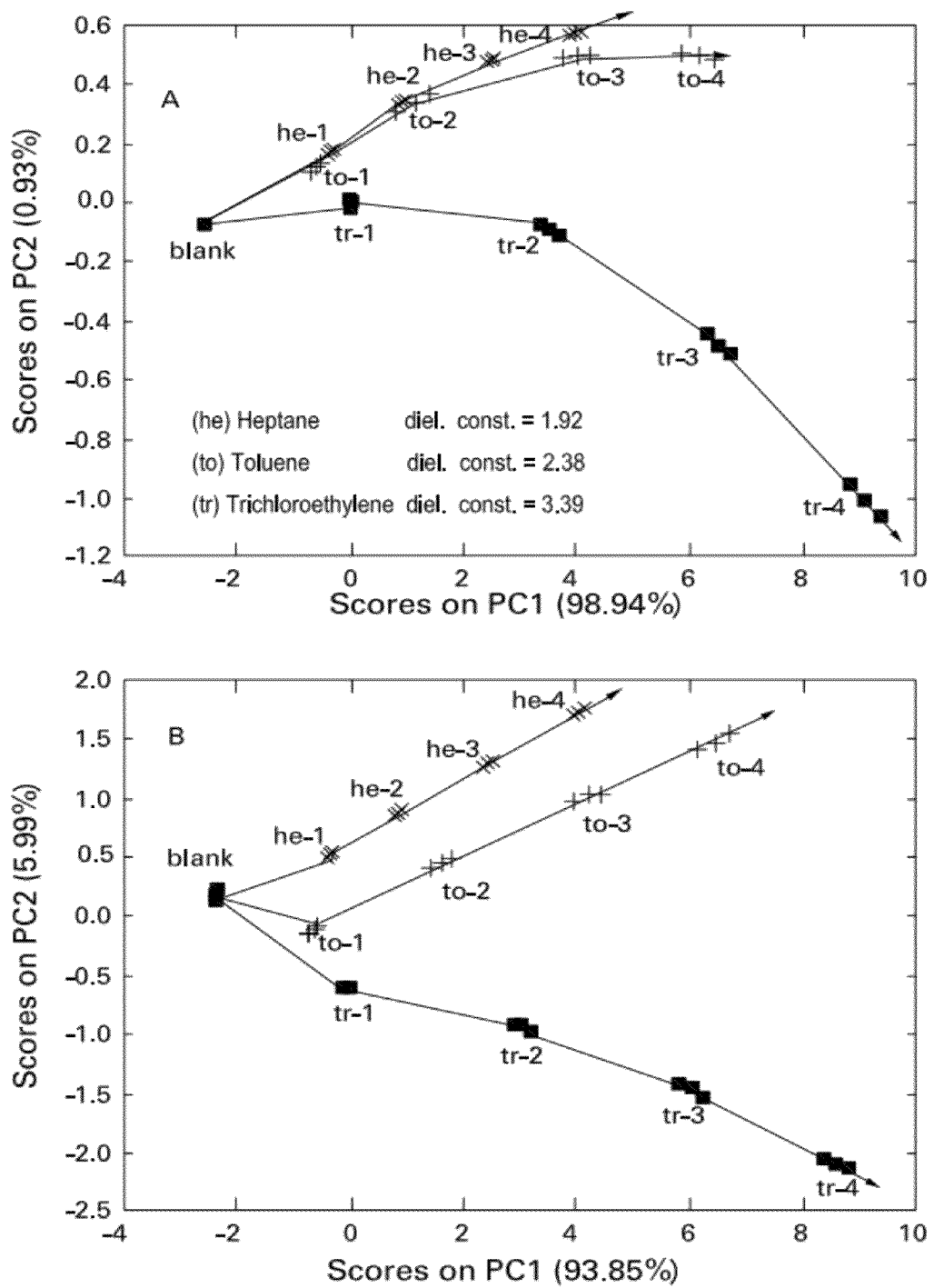

FIG. 15 illustrates results of operation of an individual resonant sensor under non-optimized (A) and optimized (B) conditions.

These and other features, aspects, and advantages of the present invention will become better understood when the following detailed description is read with reference to the accompanying drawings in which like characters represent like parts throughout the drawings, wherein:

DETAILED DESCRIPTION

Figure 7:
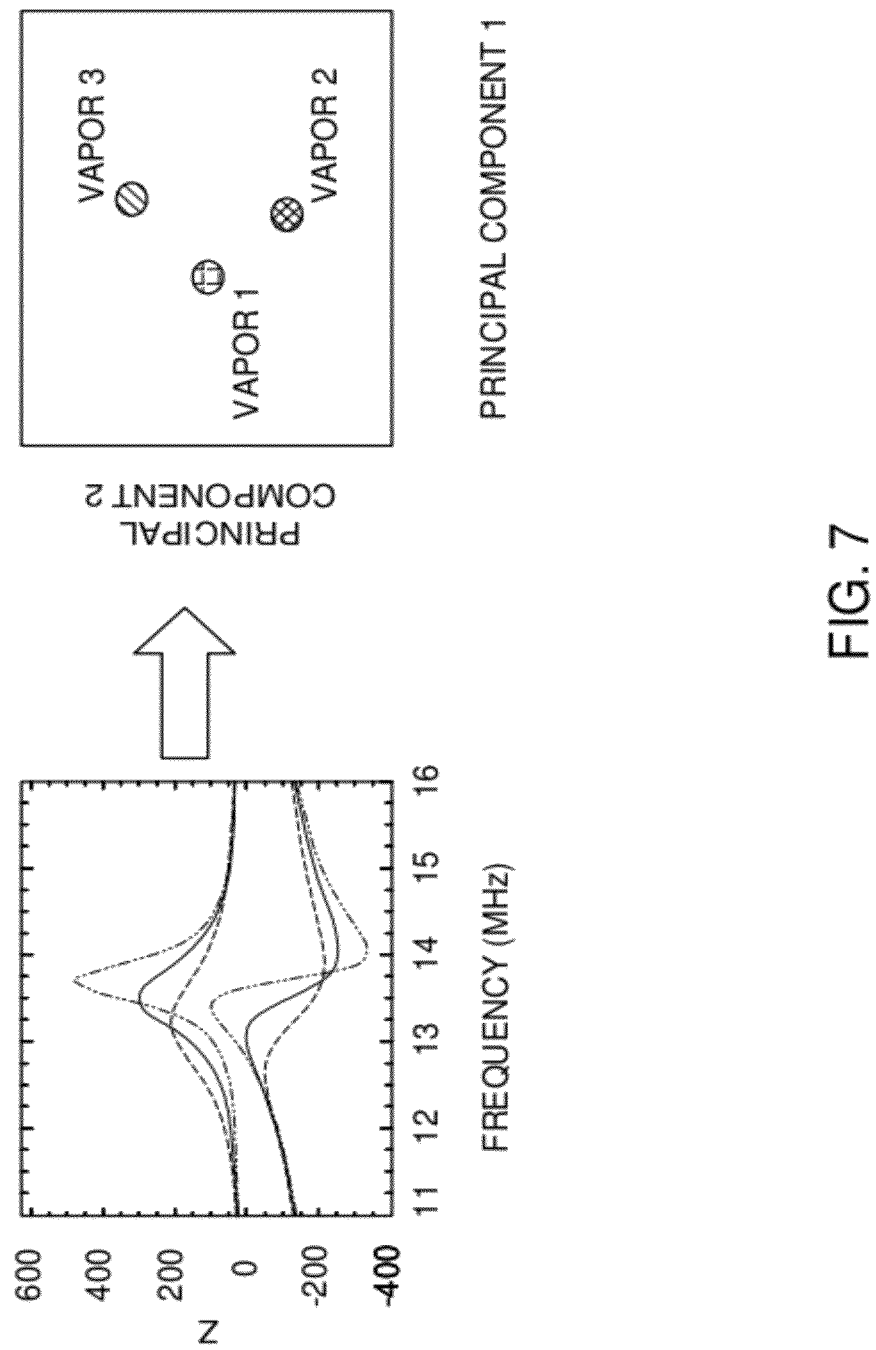
FIG. 7 is a schematic presentation of resonant complex impedance spectra of three vapors obtained using a multivariate sensor and conversion of these resonant complex impedance spectra using principal components analysis (PCA) to a response pattern of three different vapors.

The term 'multivariate sensor' is referred to herein as a single sensor capable of producing multiple response signals that are not substantially correlated with each other and where these individual response signals from the multivariate sensor are further analyzed using multivariate analysis tools to constract response patterns of exposures to different analytes and their different concentrations. In one embodiment, multivariable or multivariate signal transduction is performed on the multiple response signals using multivariate analysis tools to construct a multivariate sensor response pattern. A nonlimiting example of a response pattern of a sensor using multivariable signal transduction is shown in FIG. 7, which will be discussed in detail later in the description.

The term 'predictably affects' with respect to sensor operation is referred to herein, as when a calibration function of the sensor exists that relates the sensor response to concentration of at least one analyte through a mathematical function where one sensor multivariate output corresponds to one concentration of at least one analyte. The sensor response is predictably affected by the analyte when the calibration function of the sensor is used to calculate the analyte concentration from the sensor response.

One or more embodiments of the sensor system generally comprise at least one resonant sensor circuit comprising a sensing material having at least two material properties that change at different ratios in the presence of different analytes.

In one embodiment, the sensor circuit is configured to detect more than one analyte using at least two vapor response mechanisms of a sensing material and where the sensing material has at least two material properties that change upon exposure to one or more analytes. The sensor generates a multivariate response pattern upon sensor exposure to different analytes. The sensor may comprise resonant electronic circuits and/or resonant optical circuits.

In one embodiment, the sensor circuit is configured to detect more than one analyte using at least two inputs into an integrated circuit chip of the sensor circuit where the inputs into the integrated circuit chip are from the same or from different sensing materials. The sensor circuit generates a multivariate response pattern upon sensor exposure to different analytes. The sensor circuit provides a wireless or wired communication with the sensor user.

Figure 1:
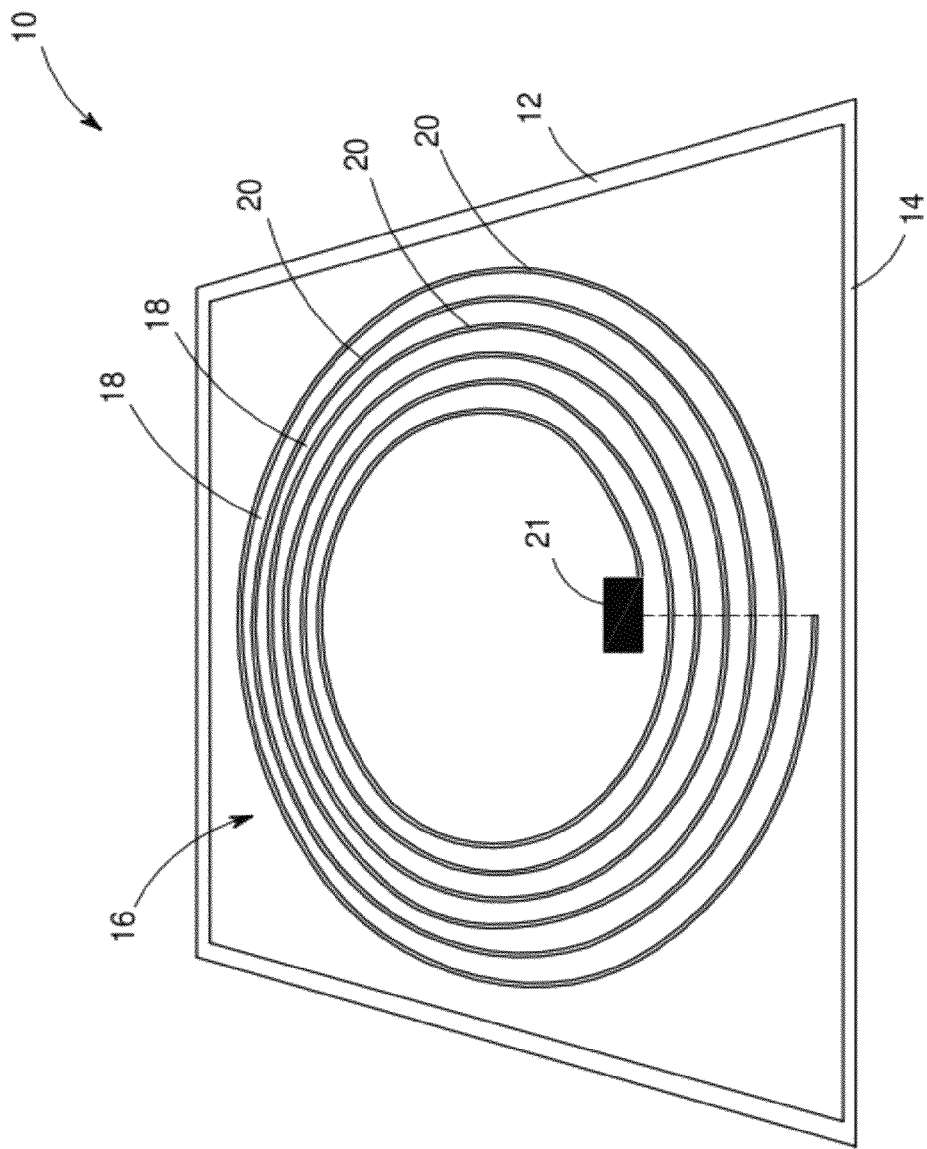
FIG. 1 is a top view of an embodiment of a radio frequency based sensor of the invention.
Figure 2:
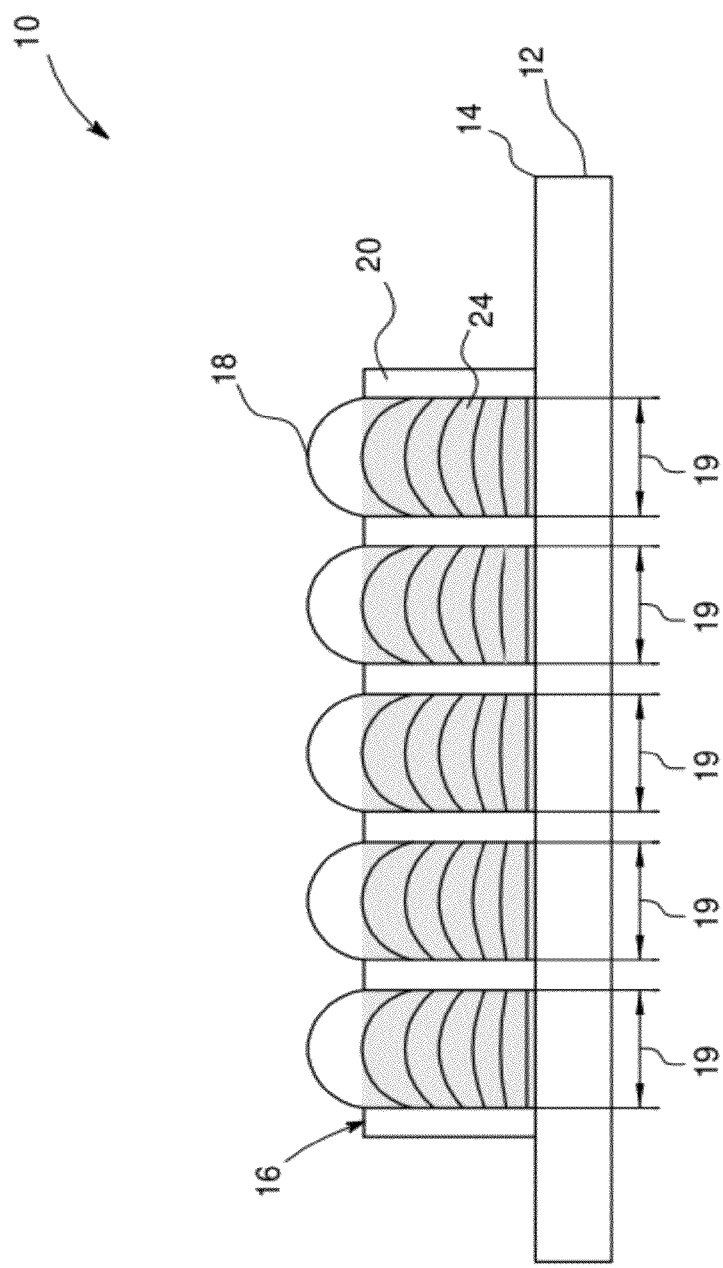
FIG. 2 is a cross-sectional view of a portion of the radio frequency based sensor of FIG. 1, wherein the sensing material is disposed between the concentric electrodes.
Figure 3:
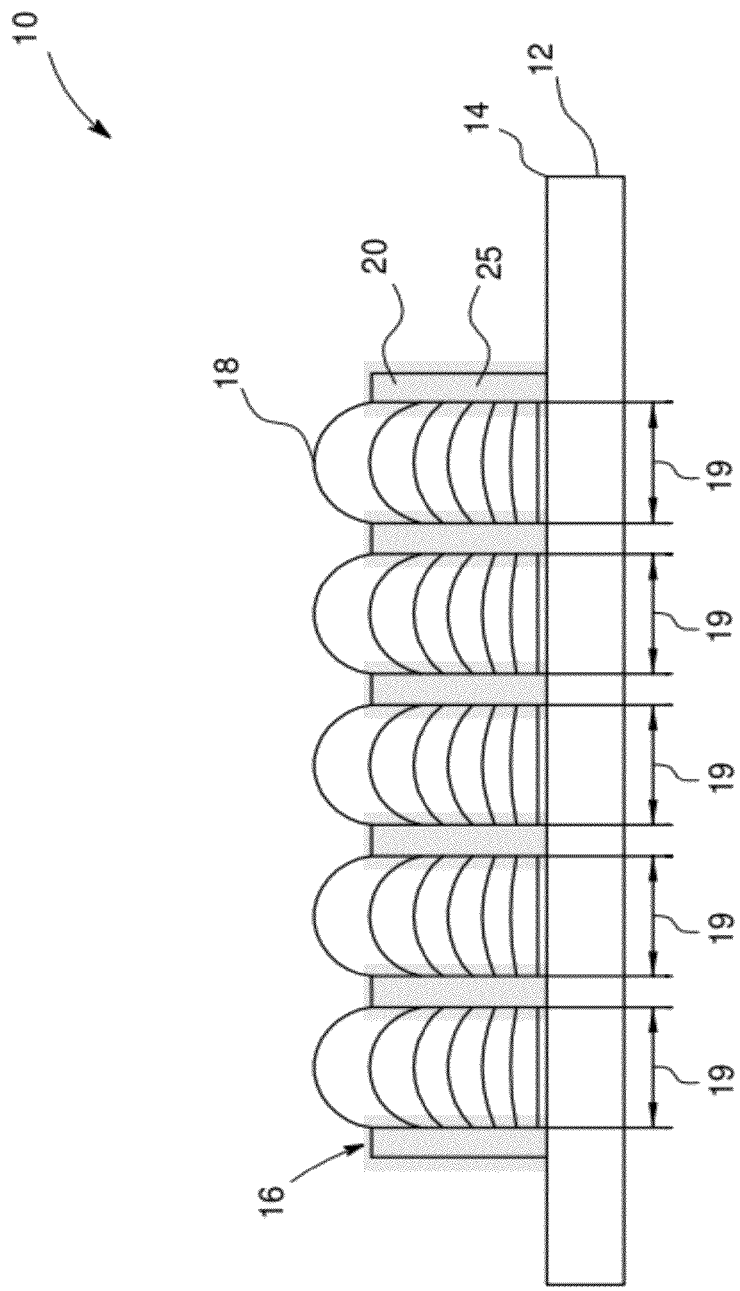
FIG. 3 is a cross-sectional view of another embodiment of a radio frequency based sensor wherein the sensing material is disposed as a coating on the concentric electrodes.
Figure 4:
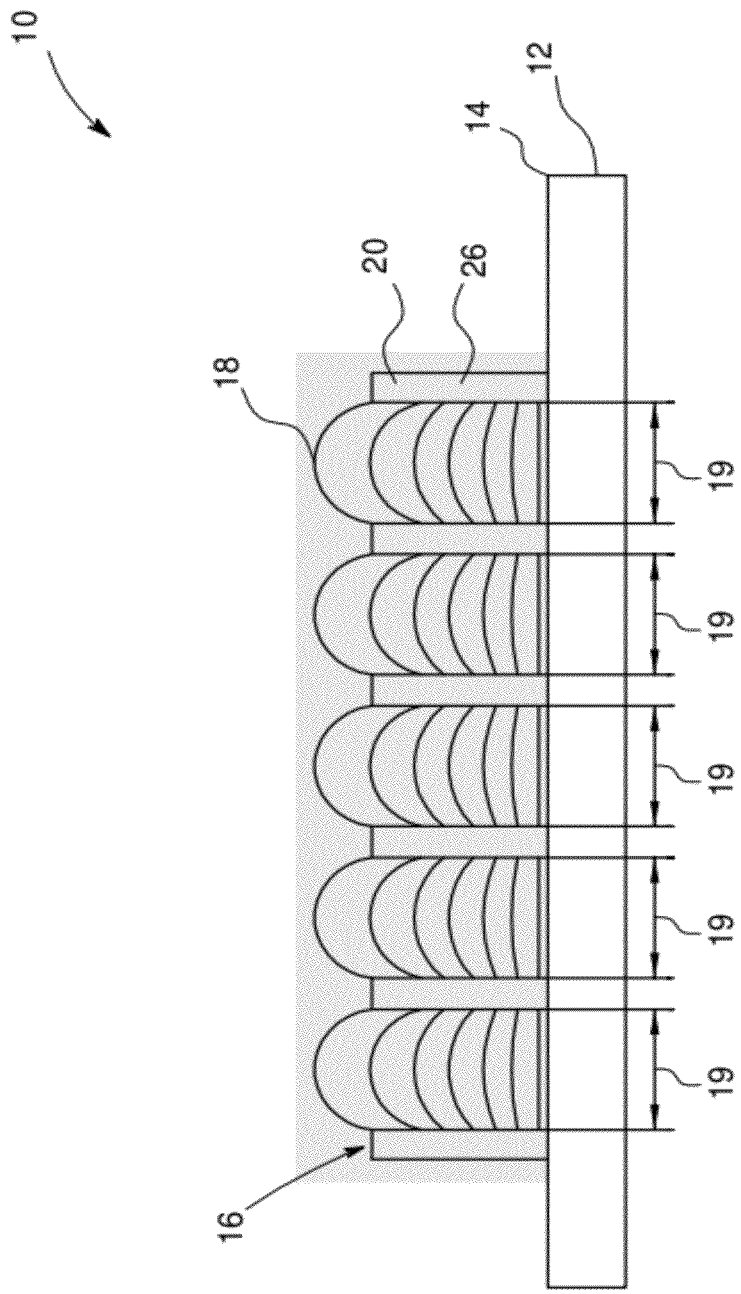
FIG. 4 is a cross-sectional view of a portion of the radio frequency based sensor of FIG. 1, wherein the sensing material is disposed between and on the concentric electrodes.

An embodiment of the sensor system is generally shown and referred to in FIGS. 1, 2 and 3 as sensor 10, and comprises a radio frequency identification (RFID) device. The sensor 10 comprises a resonance frequency sensor circuit employing a radio frequency tag 12 having a substrate 14, an antenna 16, and a chip 21. Antenna 16 is formed as a coil with essentially concentric electrodes 20 that form a coil. The chip 21 is used to store data information and is made as an integrated circuit chip. Nonlimiting examples of such data are information on the detected analyte, calibration parameters of the sensor, user defined information (manufacturing date, expiration date), authentication data. The radio frequency tag 12 induces an associated electromagnetic field 18 formed between electrodes 20. The space between electrodes 20 forms sensing regions 19. Sensing materials 24 may be present in the sensing regions 19 and may be in operative association with the substrate 14. The sensing materials 24 are capable of interacting or binding to a target analyte. In one embodiment, the sensing materials are placed in the electromagnetic field of the electrodes. In the embodiment of FIG. 2, the sensing materials 24 are disposed between the pairs of electrodes 20 in the sensing regions 19. In another embodiment, as illustrated in FIG. 3, the sensing materials 25 are disposed as a coating on the electrodes. In some embodiments, the sensing material is at least partially in contact with one of the electrodes and in other embodiments the sensing material 26 is in contact with all electrodes (FIG. 4).

In some embodiments, the chip 21 (FIG. 1) is used to accept inputs from at least two sensors, where the sensors are positioned in the proximity to the chip 21 or are the integral part of the chip 21. The chip 21 and the associated at least two sensors constitute the sensor circuit. This sensor circuit is configured to detect more than one analyte using at least two inputs into an integrated circuit chip of the sensor circuit where the inputs into the integrated circuit chip are from the same or from different sensing materials. The chip 21 generates a multivariate response pattern upon sensor exposure to different analytes. The chip 21 provides a wireless or wired communication with the sensor user. The chip 21 can be called "memory chip" or "integrated circuit memory chip."

Figure 5:
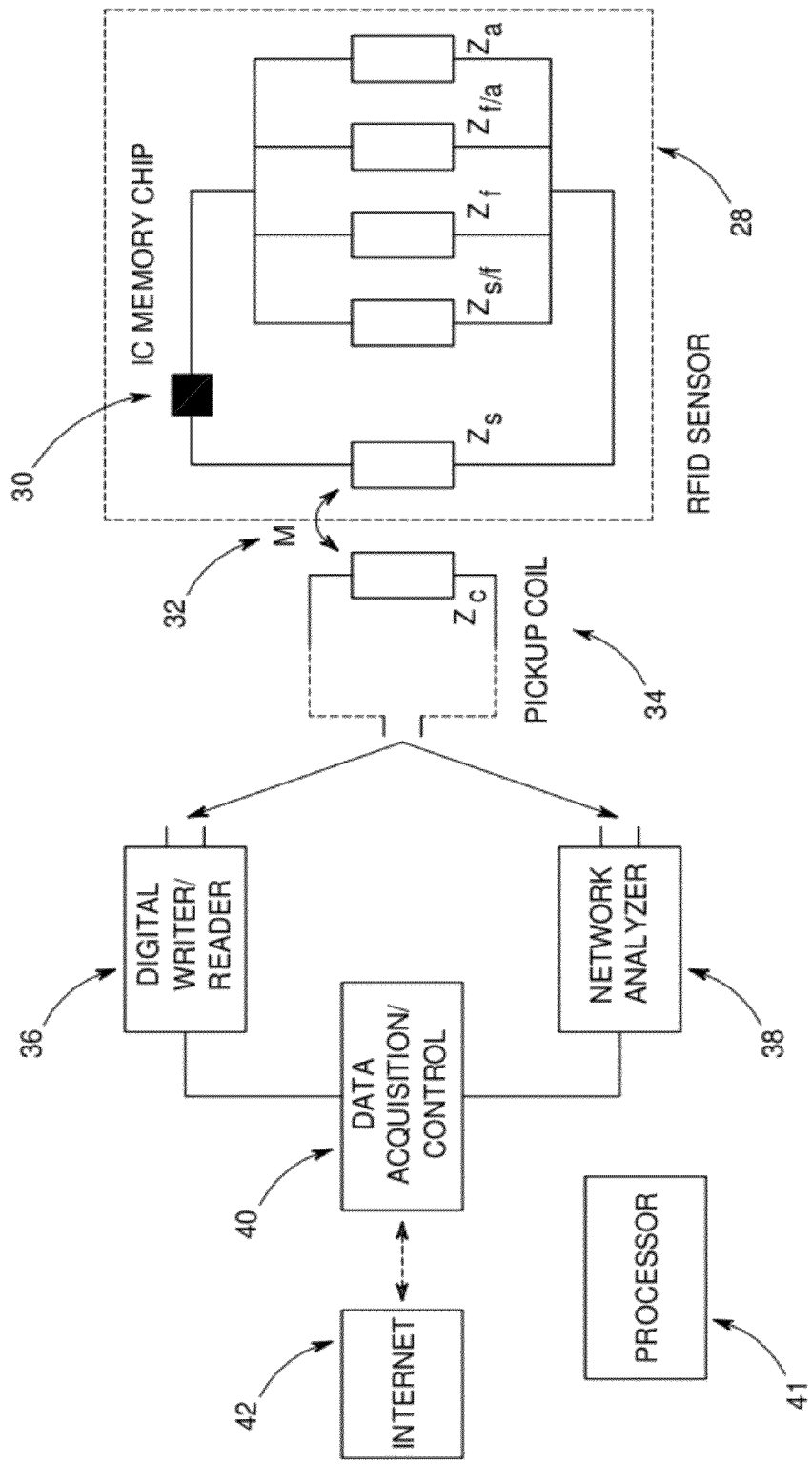
FIG. 5 is a schematic representation of operation of one of the disclosed multivariate sensors, nonlimiting example.

In some embodiments, the system or the sensor system comprises an inductor-capacitor-resistor (LCR) circuit with a resonance frequency response provided by the complex impedance (Z) of this circuit. In the most general description, four quantities, such as resistance (R), capacitance (C), inductance (L) and frequency (f), determine the complex impedance (Z) of a circuit or a circuit part. In general, the multivariate sensor has a complex impedance that includes a complex impedance of the sensor electrode structure $Z_s$, complex impedance of the sensing film $Z_f$, complex impedance of the interface between the sensor electrode structure and the sensing film $Z_{s/f}$, complex impedance of the interface between the sensing film and the analyzed fluid $Z_{f/a}$, and complex impedance of the analyzed fluid $Z_a$. The relation between $Z_s$, $Z_f$, $Z_{s/f}$, $Z_{f/a}$, and $Z_a$ is that they are as series or parallel circuits. In a non-limiting example, FIG. 5 illustrates that $Z_f$, $Z_{s/f}$, $Z_{f/a}$, and $Z_a$ are in parallel, while their combination is in series with $Z_s$ and the integrated circuit (IC) memory chip (30). The RFID sensor (28) comprises $Z_s$, $Z_f$, $Z_{s/f}$, $Z_{f/a}$, and $Z_a$ and is being interrogated with a pick up coil (34) of the sensor reader. The pick up coil has its complex impedance of the pick up coil $Z_c$. The coupling between the pick up coil and the sensor is performed through a mutual inductance coupling M (32). The total complex impedance of the sensor is measured using a network analyzer (38), while the digital information from the memory chip is measured with a digital writer/reader (36). These measurements are performed, for example, using a multiplexer. In a non-limiting example, the data acquisition and control (40) is further accomplished and data is sent via Internet (42) to an end-user. In some embodiments, a processor 41 is present in the system to generate a multivariate sensor response pattern that is based at least in part on a change in the two material properties of the sensing material. In some embodiments, a processor (41) is present in addition to the data acquisition and control 40. For example, the processor 41 may acquire the sensor and calibration data from the data acquisition and control (40) to generate the multivariate sensor response pattern, which may subsequently be sent to the end user via the Internet. Alternatively, the processor 41 may be present at the user end, and receives raw or semi-processed data through the Internet and generates the multivariate sensor response pattern.

The multivariate sensor system can also operate with or without the memory chip. The sensor system can operate over different frequency ranges where the interrogation of the sensor system can be performed using different methods known in the art with non-limiting examples of measurements in the kilo-Hertz, Mega-Hertz, Giga-Hertz, Tera-Hertz, infrared, visible, and ultraviolet range of electromagnetic frequency spectrum. In some embodiments, the sensor system is capable of operating within an electro magnetic spectrum comprises a frequency range from about $10^5$ Hertz to $10^{15}$ Hertz. Sensor system can be wireless or wired to a sensor reader. The total complex impedance of the sensor system is measured using any known measurement technique with nonlimiting examples that include frequency scanning and sensor excitation with a pulsed signal to observe the sensor ring-time. Further, depending on the particular measurement application and particular sensor design, relative contributions of $Z_s$, $Z_f$, $Z_{s/f}$, $Z_{f/a}$, and $Z_a$ may vary. The type of a sensing material affects the complex impedance of the sensing film $Z_f$. The type of a sensing material and the method of application of the sensing material onto the electrode structure of the sensor system affect the complex impedance of the interface between the sensor electrode structure and the sensing film $Z_{s/f}$. The type of a sensing material, the method of application of the sensing material onto the electrode structure of the sensor system, and the morphology of the sensing material affect the complex impedance of the interface between the sensing film and the analyzed fluid $Z_{f/a}$. The type of analyzed fluid sample (liquid or gas) affects the complex impedance of the analyzed fluid $Z_a$. In some embodiments, a processor is present in the system to generate a multivariate sensor response pattern that is based at least in part on a change in the two material properties of the sensing material. In some embodiments, a processor is an integral part of the sensor circuit or an integral part of chip 21 (FIG. 1) or a separate device.

Figure 6:
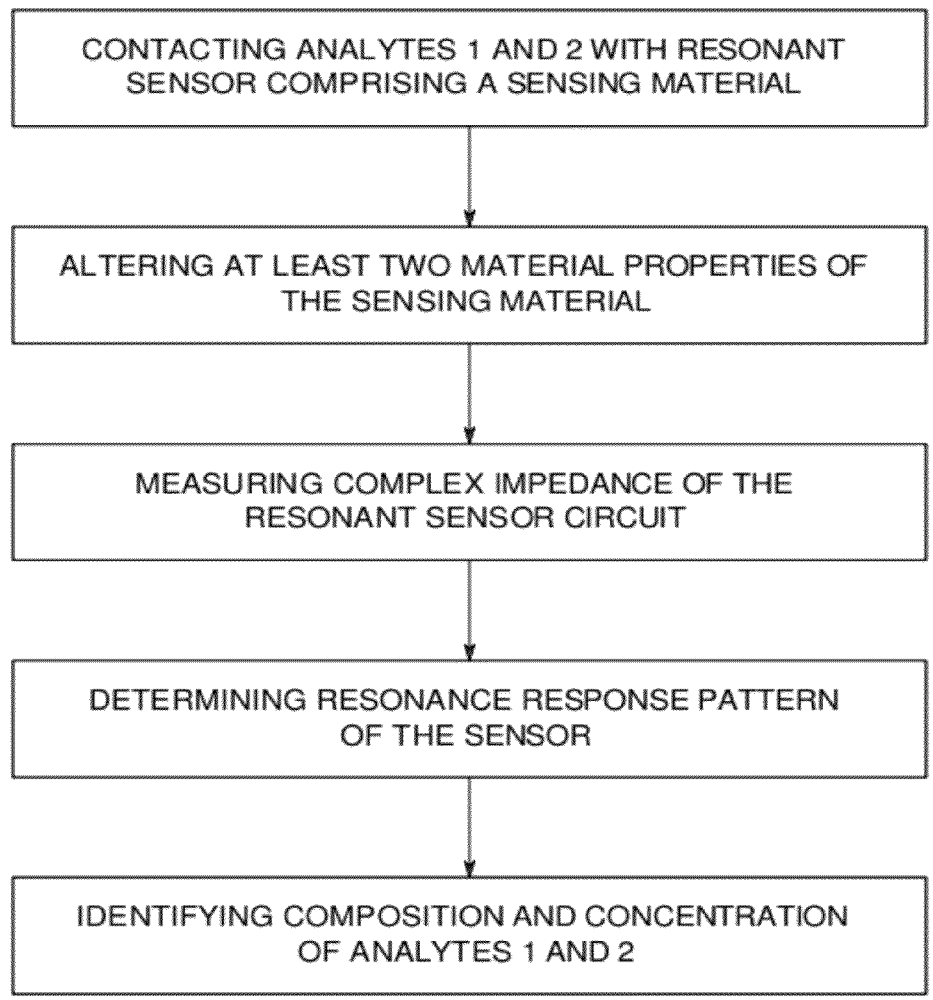
FIG. 6 is a method for selective detection of at least two analytes with one multivariate sensor.

In one embodiment, a method for selective detection of at least two analytes with one multivariate sensor system is described (FIG. 6). The method comprises the steps of contacting at least two analytes with a resonant sensor, wherein the sensor system comprises at least one resonant sensor circuit and altering at least two sensing material properties followed by measuring complex impedance response of the resonant sensor circuit, and determining a multivariate response pattern of the sensor system by performing a multivariate analysis of the complex impedance response.

Finally, from this pattern, the sensor system identifies the analytes and concentrations of at least two analytes. One of analytes may be the analyte of interest to the end-user while the second analyte may be not of interest to the end-user (an interferent) or may be another analyte also of interest to the end-user.

In another embodiment, a method for selective detection of at least two analytes with one multivariate sensor system is described. The method comprises the steps of contacting at least two analytes with a sensor circuit, wherein the sensor circuit comprises at least one integrated circuit chip that is configured to accept inputs from at least two sensors, wherein the sensors are positioned in the proximity to the chip or are the integral part of the chip; detecting more than one analyte using at least two inputs into an integrated circuit chip of the sensor circuit where the inputs into the integrated circuit chip are from the same or from different sensing materials; determining a multivariate response pattern of the sensor system upon sensor exposure to different analytes, by performing a multivariate analysis of the response of at least two sensors; identifying the analytes and concentrations of at least two analytes from this pattern, where one of analytes may be the analyte of interest to the end-user while the second analyte may be not of interest to the end-user (an interferent) or may be another analyte also of interest to the end-user; and providing a wireless or wired communication with the sensor user.

The inputs from sensors into the integrated circuit chip can be digital or analog. The digital inputs from sensors can be single-bit providing threshold measurements or multi-bit, providing high-resolution measurements. The analog inputs from sensors can be for signals such as resistance input, capacitance input, inductance input, voltage input, or current input.

The sensor circuit may operate without any assistance from a battery or with assistance from a battery, wherein the battery is a part of the sensor.

In certain embodiments, the electrode material may be adapted to transport electrical current with determined electrical properties. Nonlimiting examples of electrode materials include metals such as copper, aluminium, gold, silver, alloys of copper (e.g. brasses, bronzes), alloys of aluminum (e.g. Nambe™, Silumin™), alloys of gold (e.g. Electrum™), conducting polymers, doped conducting polymers, such as doped polyacetylene, doped polyaniline, doped polythiophene, carbon nanotubes, carbon fibers, carbon particles, carbon paste, conducting inks, or combinations thereof. In certain embodiments, the electrode material is inert to analytes. In certain embodiments, the electrode material may also provide a function of a sensing material, when, for example, electrode material is a conducting polymer, doped conducting polymer and any other material that will predictably affects sensor response.

In various embodiments, the system may include an antenna having less than one turn, one turn or more than one turn. Such an antenna may be fabricated by employing techniques, such as, but not limited to, electron-beam lithography, microlithography, nanolithography, screen-printing. The resonance sensor circuit may include additional elements such as, but not limited to, integrated circuit memory chip and capacitors. In one embodiment, the sensor system comprises a processor to generate a multivariate sensor response pattern that is based at least in part on a change in the two material properties of the sensing material.

In some embodiments, the sensing materials are applied onto a resonant sensor to induce changes in the resonant complex impedance of the sensor. The sensors use changes such as, but not limited to, dielectric, dimensional, and charge transfer, physical sorption, chemical sorption, Schottky barrier interfacial potential, electronic donation, hydrogen bonding, charge-trapping changes of sensor material properties to induce changes in resonant properties of the resonant circuit.

Non-limiting examples of analytes that may be detected by embodiments of the sensors system of the present invention include inorganic gases, volatile organic compounds (VOC), oxidizing and reducing gases, dissolved gases, biological species in water or in air or combinations thereof.

The radio frequency based sensors of the invention, may be employed in a detection system. For example, the detection system may comprise a sample delivery unit for delivering a sample to the radio frequency based sensor, and a display device, such as a monitor, for displaying the electrical signal representative of a binding event.

The sensor may be wireless, or wired, or electronic, (radio frequency identification) RFID based, non-RFID based, or combinations of two or more. In embodiments where the sensor is a RFID based sensor, the sensor may be a wireless sensor. Also, the RFID based sensor may include a passive RFID tag, or a semi-passive RFID tag, or an active RFID tag. Further, the RFID tags may be configured to operate at frequencies ranges, such as but not limited to, low frequency range from about 125 KHz to about 135 KHz, high frequency range of about 13.56 MHz, ultra high frequency (UHF) range from about 850 MHz to about 960 MHz, and microwave frequency range of about 2.45 GHz-5.8 GHz.

In one embodiment, sensors are embedded into or onto packaging labels, tickets, or banknotes. In one embodiment, sensors are embedded into or onto disposable or re-usable consumer products. In one embodiment, sensor chips have the memory size ranging from 1 bit to 1 gigabyte of memory.

Sensors are interrogated (measured) with sensor readers that can be reading analog or digital information from the sensors. Nonlimiting examples of devices with incorporated sensor readers for reading of the sensor response include a residential device, an industrial device, a home remote control, a home appliance, an industrial appliance, a device non-connected to the network, a device connected to the network, a stationary device, a mobile device, a device for public security and protection, a medical device, an industrial safety device, a food safety device, a desktop device, a pocket-size device, and an embedded device.

Nonlimiting examples of communication modes for reading of the sensors include WiFi, Bluetooth, Zigbee, near field communication (NFC), inductive coupling, capacitive coupling, optical coupling, card emulation, tag reading, peer to peer, high-frequency (HF) communication, ultrahigh-frequency (UHF) communication, ISO 15693, ISO 14443, ISO 18000-1, ISO 18000-2, ISO 18000-3, ISO 18000-4, ISO 18000-5, ISO 18000-6, ISO, 18000-6C, ISO 18000-7.

Nonlimiting examples of communication implementations include stand-off detection at distances ranging from 1 meter to 1000 kilometers, proximity detection at distances ranging from 1 micrometer to 1 meter, and non-galvanic contact detection in a "tapping" scenario for a short period of time or in a non-galvanic attachment scenario for a relatively long period of time.

Individual sensors can be arranged into a sensor network where sensors communicate with each other and with the central station or with the central station. In particular, individual sensors can be arranged into a wireless sensor network (WSN). In a WSN, individual sensors are typically arranged into wireless sensing nodes (also known as motes) with the key hardware (long-lifetime battery or energy harvesting source, simple signal conditioning components, low-power processor) and software (small needed memory, computational capacity, high modularity) requirements for individual nodes. The arrangement of individual wireless sensors into a distributed network brings new opportunities and also significant challenges to be solved first. The general challenges of WSNs for gas and physical sensing include power consumption of individual sensors and handling of massive heterogeneous data from the WSN. The inadequate selectivity of gas sensors further prevents their reliable applications in WSNs.

The opportunities for WSNs with gas sensing nodes originate from the synergistic combination of new data-generation and processing concepts with new sensor-integration concepts. Sensors arranged as networks can significantly benefit from novel data-generation and processing concepts currently unavailable for individual sensors. Three main aspects of these advantages are (1) the ability for efficient sensors communications, (2) improvement of detection accuracy through data fusion, and (3) opportunities for automatic re-calibration of individual sensors on the network.

The broad opportunities for WSNs originate from the capabilities based on concepts of integration of individual sensors to form sensing nodes in a WSN. Indeed, a stationary or mobile origin of sensing nodes would dictate the diversity of application scenarios for a WSN. Significant advantages in the reliability and accuracy of a WSN performance is achieved upon an integration of sensing nodes into a component or a system that already has a maintenance schedule that is matched to a maintenance schedule for sensing nodes.

As a result of developments in the data-generation/processing and sensing node-integration concepts, the application concepts for WSNs can be broadly described as those that rely on (1) stationary sensing nodes for mapping of chemical sources, (2) mobile sensing nodes for dynamic localization of chemical sources, (3) real-time chemical condition monitoring of high-value goods and their associated storage conditions, and (4) combination of sensing nodes with an intelligent inventory management.

The key features of wireless sensor networks are in two areas such as (1) data-generation and processing concepts and (2) sensor-integration concepts. In the area of data-generation and processing concepts, the key WSN features include: numbers start below 1. Implementation of available infrastructure for communications of sensors;
2. Heterogeneous sensors coupled to multiparameter coincidence techniques to improve detection accuracy;
3. Fusion and processing strategies for massive and dynamic data from WSNs for time-critical decision-making and for providing ability to identify spurious signals and malfunction of individual sensors on the network;
4. Data acquisition algorithms for individual sensors to reduce power consumption and to extend operational lifetime before battery replacement;
5. Auto-calibration methods for maintenance-free operation of individual gas sensors in WSN. Responses of sensors are calibrated against local reference monitoring stations;
6. Internet-enabled pollution monitoring server interfaced to Google Maps to display real time pollutants levels and locations in large metropolitan areas.

In the area of sensor-integration concepts, the key WSN features include:
1. Integration of sensors into mobile phones;
2. Autonomous sensor- and GPS-equipped mobile robotic devices for location and validation of pollution, homeland security threat, and other sources;
3. Integration of sensors into public or personal transportation vehicles for pollution and homeland security threat monitoring with a significant benefit of matching vehicle/sensor maintenance schedules.

In one embodiment, nonlimiting examples of sensing material comprises carbon nanotubes, metal oxide nanotubes, semiconducting nanotubes, mixture of semiconducting and metallic nanotubes, graphene, functionalized nanotubes, functionalized graphene, nanoparticles, nanowires, nanoribbons, or nanosheets, biological sensing materials such as nucleic acids, aptamers, antibodies, peptides, carbohydrates and others, that are functionalized or not functionalized with labels (molecules or nanoparticles) to promote more than one sensing material property. In one embodiment, the sensing material is an electronic material. In one embodiment, the sensing material is an organic electronic material. In another embodiment, the sensing material is an organic electronic polymer, such as, but not limited to conjugated polymers and intrinsically conducting polymers. In some embodiments, the polymer sensing material is a copolymer sensing material and in other embodiments, the sensing material is a homopolymer sensing material. Some sensing materials include rigid copolymers and other sensing materials include flexible copolymers. Other examples of sensing materials include, but are not limited to, homopolymers and co-polymers of fluorenes, carbazoles, and triarylamines with rigid and flexible links. These classes of polymeric sensing films may be adapted to a given application by designing polymers with the appropriate side chains and end groups.

Organic electronic polymers are sensitive to environmental perturbation because of their electrical transport properties and energy migration. The electrical transport property of organic electronic polymers is a material bulk transport property and as a result, the response of this material property can be more sensitive than potentiometric and amperometric methods that are dependent on local electronic structure. Organic electronic polymers have the ability to amplify response to an analyte binding event. This amplification is due to the efficient energy transfer in organic electronic polymers that allows excitation energy from large areas to be effectively funneled into the analyte binding sites.

Organic electronic polymers, in various embodiments, provide detection of analytes using one or more simultaneous vapor-response mechanisms such as changes in density of charge carriers, changes in mobility of charge carriers, conformational transitions of polymer chain, and polymer swelling. The design of the contributions of these response mechanisms to the overall response of the sensing materials results in the creation of response patterns of various analytes by the synthesized polymers. These and other response mechanisms can be also used for detection of analytes in liquids, where analytes in liquids can be proteins, nucleic acids, viruses, cells, bacteria, spores, toxins.

In one embodiment, non-limiting examples of sensing materials comprise ligand-protected metal nanoparticles films. The ligands that protect individual metal nanoparticles are broadly divided into two classes. One class of ligands has soft linkers that change their length as a function of the amount of sorbed species (chemical species, biological species, analyte, interference, or both). With these linkers, film swelling upon exposure to species causes an increase in the film resistance with increased interparticle surface-to-surface separation. The dielectric constant of these films can also either increase or decrease depending on the dielectric constant of the species causing resistance changes. The other class of ligands has rigid linkers that restrain swelling of sensing films and boost the effects of species-dependent changes of the dielectric constant of the film.

Non-limiting examples of soft linkers utilized with metal nanoparticles include poly(propyleneimine) dendrimers, polyphenylene dendrimers, and n-octanethiol ligands. Nonlimiting examples of rigid linkers utilized with metal nanoparticles include 4-staffane-3,3'-dithiol and 4,4'-terphenyldithiol ligands. Nonlimiting examples of metal nanoparticles functionalized with ligands include gold, silver, platinum, palladium, alloys thereof, highly conductive metal nanoparticles, or any combination thereof.

A sensing material can be formulated with an additive to improve the sensor performance. Nonlimiting examples of the sensor performance include sensor stability, sensor sensitivity, sensor selectivity, sensor dynamic response, adhesion of the sensor film to the sensor surface, and others. Nonlimiting examples of additives include carbon black particles, carbon nanotubes, adhesion promoters, and thermal stabilizers.

Multivariate calibration methods offer several advantages over univariate calibration methods. Signal averaging is achieved since more than one measurement channel is employed in the analysis. Also, the concentrations of multiple species may be measured if they are present in the calibration samples. A calibration model is built by using responses from calibration standard samples.

As a nonlimiting example of multivariate analysis, principal components analysis (PCA) can be used to extract the desired descriptors from the measured data such as complex impedance spectra data. PCA is a multivariate data analysis tool that projects the data set onto a subspace of lower dimensionality with removed colinearity. PCA achieves this objective by explaining the variance of the data matrix in terms of the weighted sums of the original variables with no significant loss of information. These weighted sums of the original variables are called principal components (PCs). Upon applying the PCA, the data matrix is expressed as a linear combination of orthogonal vectors along the directions of the principal component.

One skilled in the art can apply the PCA analysis to complex impedance spectra collected using a multivariate sensor (FIG. 7). The resonant complex impedance spectra are first measured using the sensor for three analytes (vapors), followed by conversion to a response pattern of responses to three vapors. For example, individual responses from the sensor with the multivariable signal transduction upon exposure to analyte A1 with its certain concentration C1 are mathematically combined into a response pattern A1C1; individual responses upon exposure to analyte A1 with its other certain concentration C2 are mathematically combined into a response pattern A1C2; or exposures to another analyte A2 with it different concentrations C1 and C2 produce response patterns A2C1 and A2C2. In one embodiment, a sensor with the multivariable signal transduction should have non-overlapping response patterns to different analytes and their concentrations in order to be used to detect different analytes and their different concentrations. The response pattern shows (FIG. 7) results of PCA of three vapors demonstrating good selectivity.

In one embodiment, the multivariable sensor of this invention produces at least three orthogonal responses defined as the number of orthogonal axes after the multivariate analysis that contains the analyte-relevant information and correlates with the concentration of detected analyte.

In one embodiment, the multivariable sensor of this invention produces at least four orthogonal responses defined as the number of orthogonal axes after the multivariate analysis that contains the analyte-relevant information and correlates with the concentration of detected analyte.

Mixtures of analytes are selectively detected with an individual sensor using multivariate analysis of $\check{Z}(f)$ spectra or calculated parameters to perform classification and quantitation. Classification is performed to correctly determine the type of the analyte. Quantitation is performed to correctly determine the concentration of the analyte. Examples of classification methods include but are not limited to Principal Component Analysis (PCA), Independent Component Analysis (ICA), Linear Discriminant Analysis (LDA), and Support Vector Machines (SVM) algorithm. Nonlimiting examples of methods for performing analyte quantitation to determine the concentration of a particular analyte in a mixture include Principal Component Regression (PCR) and Independent Component Regression (ICR). In certain aspects of the invention, an SVM algorithm followed by PCR is used for classification and quantitation of a mixture of analytes.

The high degree of orthogonality of the response of the invented multivariable sensors provides the ability to reject interferences that the sensor was not previously calibrated for, referred to here as "unknown interferences." For example FIG. 14 illustrates that a single sensor provides independent quantitation of a two analytes such as toluene and tetrahydrofuran in the absence and in the presence of increasing number of interferences such as water, acetonitrile, acetone, methyl salicylate, ethanol, 1-pentanol, 1-propanol, and salicylaldehyde vapors. This capability became possible because the detected analytes had their dielectric constants different and larger than the dielectric constants of interferences.

Nonlimiting examples, of the types of interferences that are important for their rejection include environmental, industrial, food spoilage, breath volatiles interferences.

Additional nonlimiting examples of interferences are related to their chemical and physical characteristics such as the complex permittivity ($\epsilon'_r - j\epsilon''_r$) of the interference fluid such as gas, solid or liquid. The real part $\epsilon'_r$ of the complex permittivity of the fluid is also known as dielectric constant. The imaginary part $\epsilon''_r$ of the complex permittivity of the fluid is directly proportional to its conductivity σ.

The orthogonality of the sensor response is also enhanced by the control of the sensor excitation conditions. In this invention, this control is provided by the mutual inductance between the wireless sensor and the pick-up coil of the sensor reader (network analyzer). The proper selection of the sensor excitation conditions gives the ability to discriminate between closely related analytes. FIG. 15A illustrates that under non-optimized conditions, vapor of heptane (he) of dielectric constant of 1.92 cannot be reliably discriminated from vapor of toluene (to) of dielectric constant of 2.38. These vapors can be only discriminated from vapor of trichloroethylene (tr) of dielectric constant of 3.39. FIG. 15B illustrates that under optimized conditions, vapor of heptane (he) is reliably discriminated from vapor of toluene (to) and vapor of trichloroethylene (tr). This figure illustrates scores plots upon the principal components analysis (PCA) of multivariable response of an individual sensor coated with a ligand-protected metal nanoparticles film. "Blank" signifies exposure of the sensor to a carrier gas (nitrogen) and other data points (three data points per cluster) represent exposures of the sensor to four concentrations of vapors. The concentrations were 0.044, 0.089, 0.13, and 0.18 P/Po, wherein Po is the saturated vapor pressure of tested vapor and P is its partial pressure during the test.

The non-optimized condition of sensor operation is when the imaginary portion of the sensor impedance has all positive values of response. The optimized condition of sensor operation is when the imaginary portion of the sensor impedance has negative values of $Z_2$ response.

In some embodiments, the synthetic strategy for sensing materials includes the synthesis of homo-polymers and co-polymers based on their monomer composition and their inherent functional groups. Unlike the synthesis of classical sorbing polymers for VOC (volatile organic compound) detection, wherein the composition of monomers and their functional groups can only alter the partition coefficient of the VOC into the polymer film, these types of changes in monomer composition and functional groups for conjugated polymers significantly alter the vapor-response mechanisms. For example, in one embodiment, the presence of several simultaneous vapor-response mechanisms in a single conjugated polymer sensing material is one of the enablers that differentiate some of the sensing materials from classic vapor-sorbing sensing materials employed in many other sensors.

A sorbing polymer for vapor detection is a polymer wherein the composition of monomers and their functional groups can only alter the partition coefficient of the vapor into the polymer film (uptake the vapor by polymer) and does not detectably change density of charge carriers, changes in mobility of charge carriers, polymer protonation, polymer deprotonation.

Organic electronic materials that may be used in the sensor and method embodiments of the present invention have diverse charge transporting properties, energy band-gaps, and high operational stability. In some embodiments, these properties are controlled through chemical synthesis and design by: (1) altering the structure and composition of the pendent functional group "R", (2) preparing blended co-polymers whereby the electronic properties are controlled by the relative ratios of each monomer, and (3) altering the rigidity of the backbone by selecting an appropriate chemistry to link monomers or oligomers together which can ultimately control the polymer's film morphology.

In addition, the effects of the linking chemistry in making polymeric materials with flexible links are important. The linking chemistry of the polymers controls the ability of an analyte to diffuse into the conductive network. In some other embodiments, the permeability of the sensing material to analytes is altered by making the backbone of the polymer more flexible. In various embodiments, the flexible links are based on diphenylpropanes (DPP) and its derivatives. In other embodiments, the addition of fluorene (F) containing substituents to the flexible links of the polymers influences their dielectric constant, stability, selectivity against moisture, and increases the solubility relative to their non fluorinated analogues. Nonlimiting examples of links are DPP, 4F-DPP, 6F-DPP, and 10E-DPP. These molecules provide diversity in sensor response by incorporating fluorene into the flexible segments.

Non-limiting examples of functional groups that are employed with the polymers in the sensing materials of the present invention are presented in Table 1. These functional groups have diverse vapor-interaction abilities that may facilitate sensing efficiency. Using these functional groups, the conjugated co-polymers are tailored to additionally modify the charge-carrying co-polymer network to respond to a particular analyte.

TABLE 1

Vapor-interaction abilities of functional groups of conjugated polymers.

| Pendant functional group | Available interaction for sensing | Examples of available functional group | Example of sensed analyte |
| --- | --- | --- | --- |
| Alkyl | van der Waals | alkanes, ethers, tertiary amines | nonpolar aprotic (benzene) |
| Aryl | π-π stacking | electron-rich and electron poor aromatic rings | nonpolar and aromatic (benzene, toluene, chlorinated benzenes) |
| Halogen | Inductive | perfluorinated | fluorinated and halogenated ($CH_2Cl_2$, $CHCl_3$, TCE) |
| Polar protic | Hydrogen bonding | carboxylic acids, amides, amines, alcohols | polar protic and aprotic (acetonitrile, acetone, ammonia) |
| Polar aprotic | van der Waals, hydrogen bonding | Esters, ethers, tertiary amine | polar protic (MeOH, EtOH, water) |

The following examples provided are not intended to limit the invention, as defined in the appended claims, in any manner.

In each of the examples, resonant sensors were fabricated by coating the sensing region of an antenna structure with a sensing material comprising one or more groups of organic electronic polymers: flexible polymers, rigid co-polymers, and rigid homo-polymers or oligomers or a ligand-protected metal nanoparticles film. The sensing materials were applied onto the resonant antenna by a conventional draw-coating process or by a drop casting. Measurements of the complex impedance of RFID sensors were performed with a network analyzer (Model E5062A, Agilent Technologies, Inc. Santa Clara, Calif.) under computer control using LabVIEW. The network analyzer was used to scan the frequencies over the range of interest and to collect the complex impedance response from the RFID sensors. For gas sensing, generation of different concentrations of vapors was done using a computer-controlled vapor-generation system. Collected complex impedance data was analyzed using KaleidaGraph (Synergy Software, Reading, Pa.) and PLS_Toolbox (Eigenvector Research, Inc., Manson, Wash.) operated with Matlab (The Mathworks Inc., Natick, Mass.).

EXAMPLES

Example 1

Figure 8:
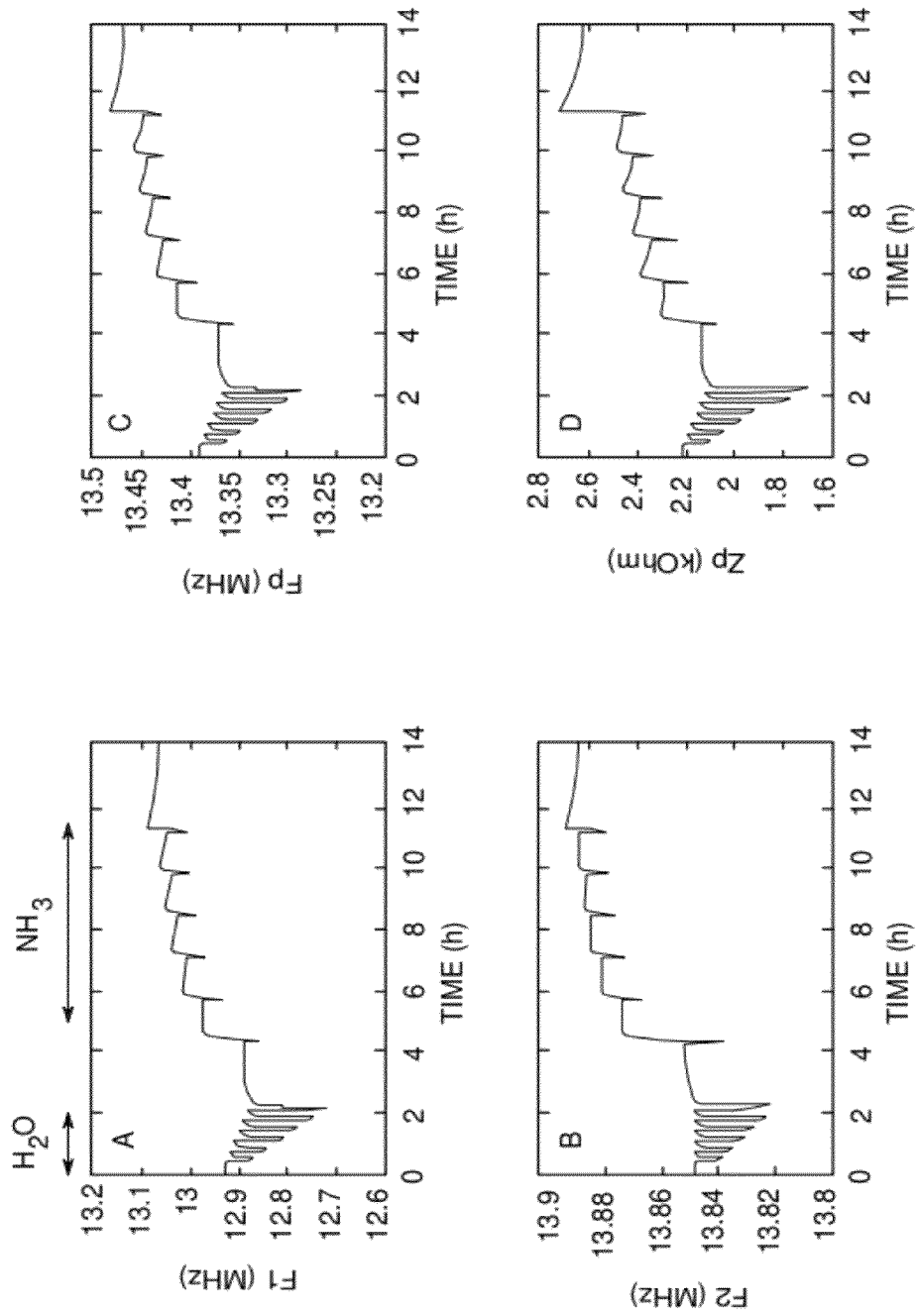
FIG. 8 is a selective analysis of $NH_3$ and $H_2O$ vapors using a single resonant multivariate sensor. (A-D) Sensor responses $F_1$, $F_2$, $F_p$, and $Z_p$, respectively upon exposures of sensor to $H_2O$ vapor (630, 1260, 2205, 3150, 4410, and 6300 ppm) and to $NH_3$ vapor (4, 8, 14, 20, 8, and 40 ppm).

As an example, polyaniline (PANI) polymer was selected to create a response pattern of various analytes when PANI is deposited onto the resonant sensor with the multivariate signal transduction. It is known that the response mechanism of PANI to $NH_3$ involves polymer deprotonation, while the response mechanism to $H_2O$ involves formation of hydrogen bonds and swelling. Results of sensor exposures to $NH_3$ and $H_2O$ vapors are presented in FIG. 8. Deprotonation of the film upon $NH_3$ exposures resulted in the increase in film impedance $Z_p$ and shifts of the sensor resonance $F_p$, $F_1$, and $F_2$ to higher frequencies. The formation of hydrogen bonds and swelling of the polymer upon $H_2O$ exposures resulted in the decrease in $Z_p$ and shifts of $F_p$, $F_1$, and $F_2$ to lower frequencies. Measurements of multiple output parameters from a single sensor revealed different recovery kinetics of responses $Z_p$, $F_1$, $F_2$, and $F_p$ during experiments with $NH_3$. Responses $Z_p$, $F_1$, and $F_p$ showed a partial recovery from $NH_3$, while $F_2$ response was irreversible with only 1.2-3.5% signal recovery.

Example 2

A poly(fluorene)-DPP copolymer (PFDPP), a flexible polymer, was used as the sensing material. The structure of the copolymer is given by the below structure:

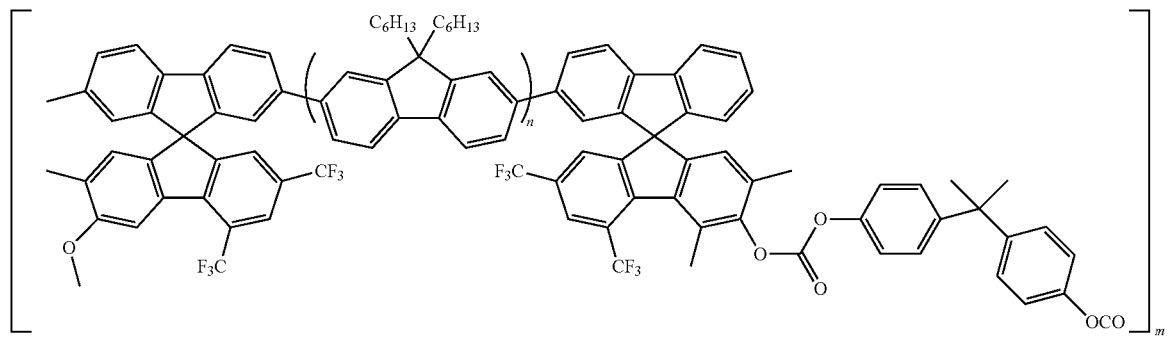

Figure 9:
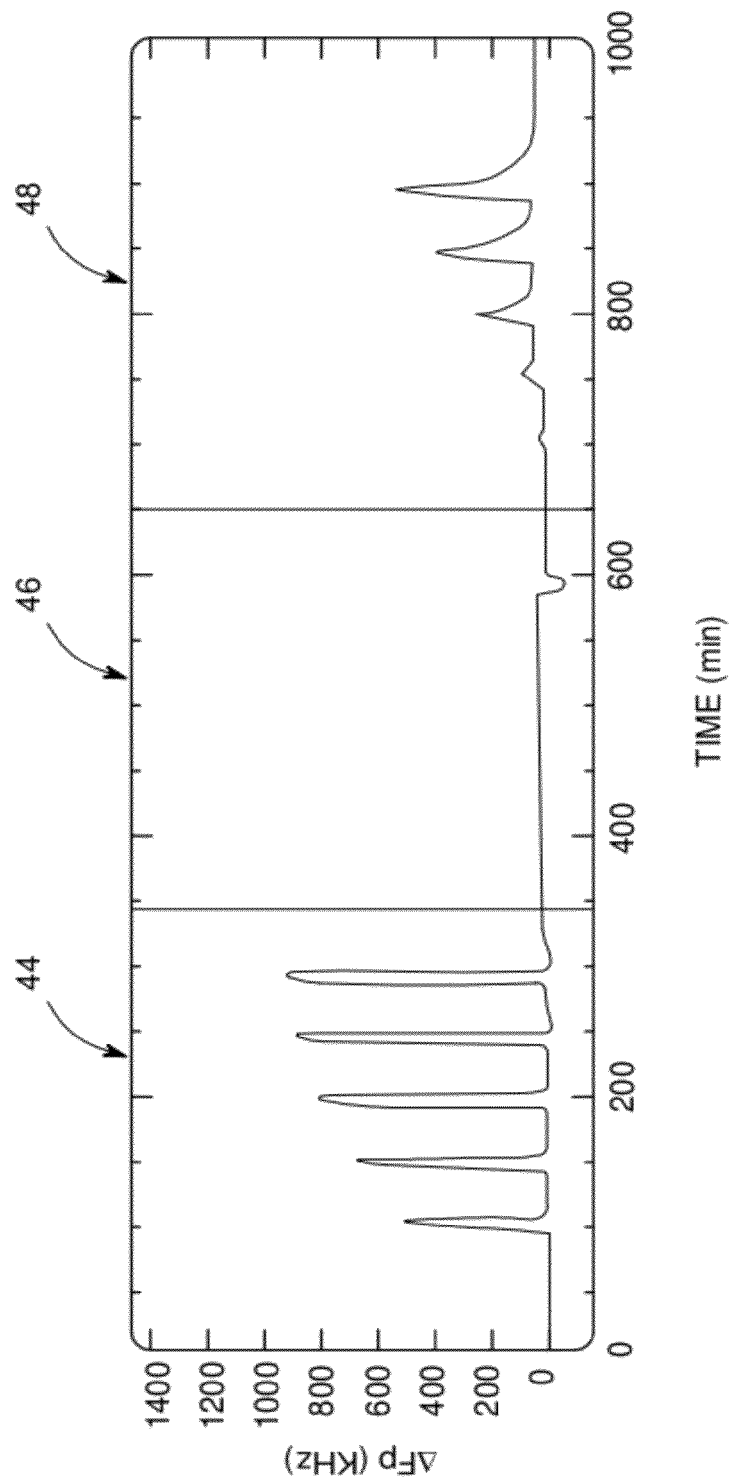
FIG. 9 is a graph showing a sensor response to a change in frequency ($\Delta Fp$) for samples of tetrachloroethane (TCE) (44), water (46) and toluene (48), wherein the sensor material of this example comprises a poly(fluorene)-diphenylpropane conjugated copolymer.

This copolymer was used to test the response for analytes such as trichloroethylene (TCE), toluene and water vapor. FIG. 9 line plots 44, 46, 48 illustrate the variation with time in the observed resonance frequency with the introduction of TCE, toluene and water vapor respectively. The observed response to TCE at the lowest tested concentration of 0.02 P/Po was 20 times stronger than the response to toluene, wherein Po is the saturated vapor pressure of tested vapor and P is its partial pressure during the test. Furthermore, response to 0.02 P/Po of TCE was about 10 times stronger than response to the highest tested water vapor concentration of 76% RH and the signal response to water was in the opposite direction than to TCE or toluene.

Figure 10:
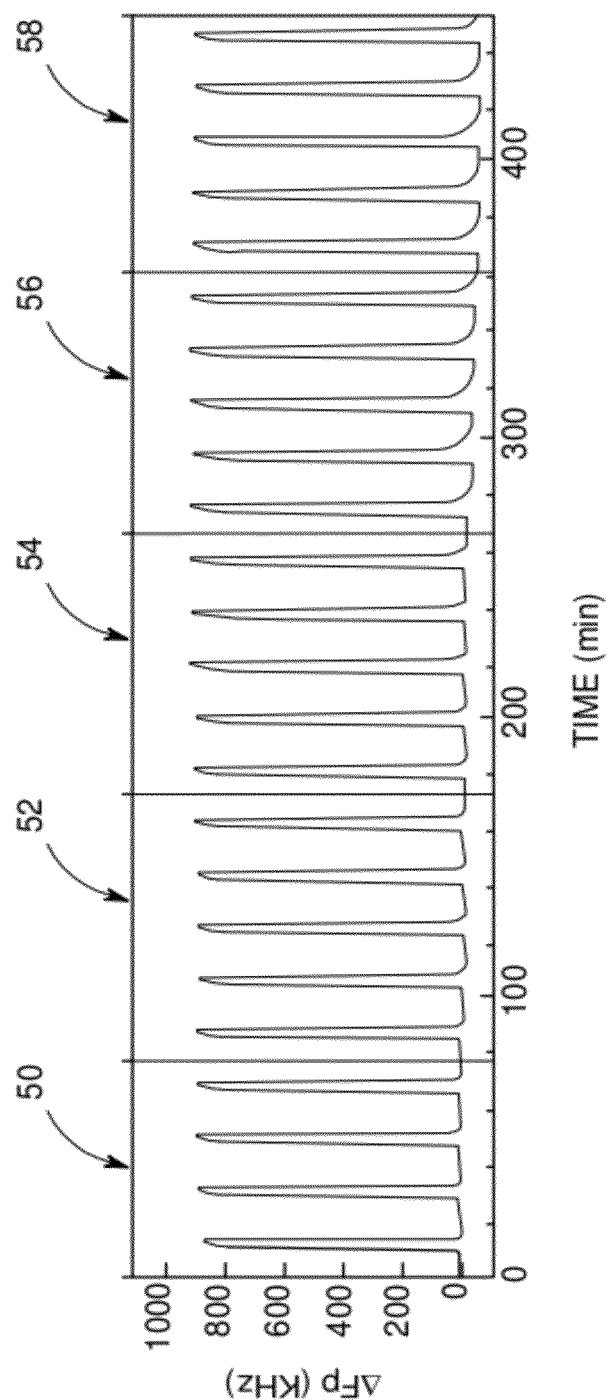
FIG. 10 is a graph showing a sensor response to a change in frequency ($\Delta Fp$) for replicate exposures of a sample of toluene at various humidity levels, 0% RH (50), 22% RH (52), 44% RH (54), 65% RH (56), 76% RH (58) wherein the sensor material of this example comprises a poly(fluorene)-polycarbonate conjugated copolymer. RH is relative humidity.

In some embodiments, the conjugated PFDPP copolymer also showed good response stability over several weeks of testing. PFDPP copolymer was also tested for repetitive response to 0.1 P/Po of TCE vapor mixed with a variable-humidity carrier gas over the wide range of humidity from 0 to 76%. In some embodiments, as illustrated by the measurements shown in FIG. 10, the sensing film did not change the response magnitude to TCE even at high humidity. Regions 50, 52, 54, 58, 58 in FIG. 10 correspond to relative humidity (RH) levels of 0, 22, 44, 65, 76% RH respectively. The detection limit (S/N=3) for TCE was calculated to be 1.2 ppm. This detection limit was an improvement of 10 to 20 times over other conventional materials employed with the same RFID antenna structures. The properties of the functional group and the particular chemistry used to link the conductive polymers together determine the VOC response.

Example 3

A homo-polymer of triarylamines (PTA), a rigid homo-polymer, was used as the sensing material. The structure of the conjugated homopolymer is given by the structure below:

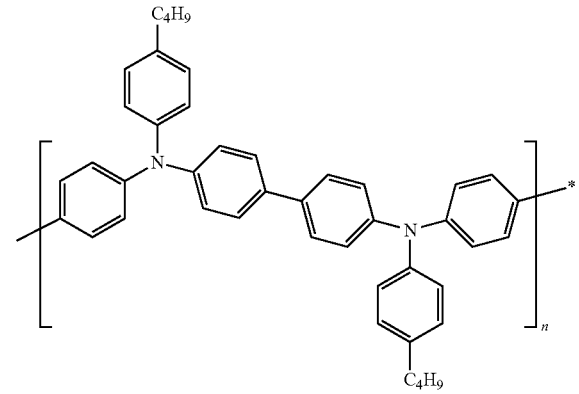

Unlike trichloromethane, the solubility of PTA in dichloromethane was very poor. The selectivity of this polymer was tested in response to trichloromethane and dichloromethane vapors while water vapor was used as an interference (FIG. 11). An examination of the baseline corrected Zp (complex impedance) response for water (line plot 60), trichloromethane (line plot 62) and dichloromethane (line plot 64) shows a signal decrease upon exposure to all tested vapors. The Fp response to water vapor (66) even at 76%RH was almost undetectable, while response to trichloromethane vapor (line plot 68) showed an increase in signal. The response to dichloromethane vapor (line plot 70) showed a decrease in signal.

Other some embodiments describe, several other candidates for the selectivity to trichloromethane/dichloromethane are co-polymers of carbazoles and triarylamines.

Example 4

A co-polymer of fluorenes (80%) and triarylamines (20%) (PFT), which is a rigid copolymer, was used as the sensing material. Experiments with a rigid co-polymer were performed with PFT and the structure of PFT is given by structure (3) below.

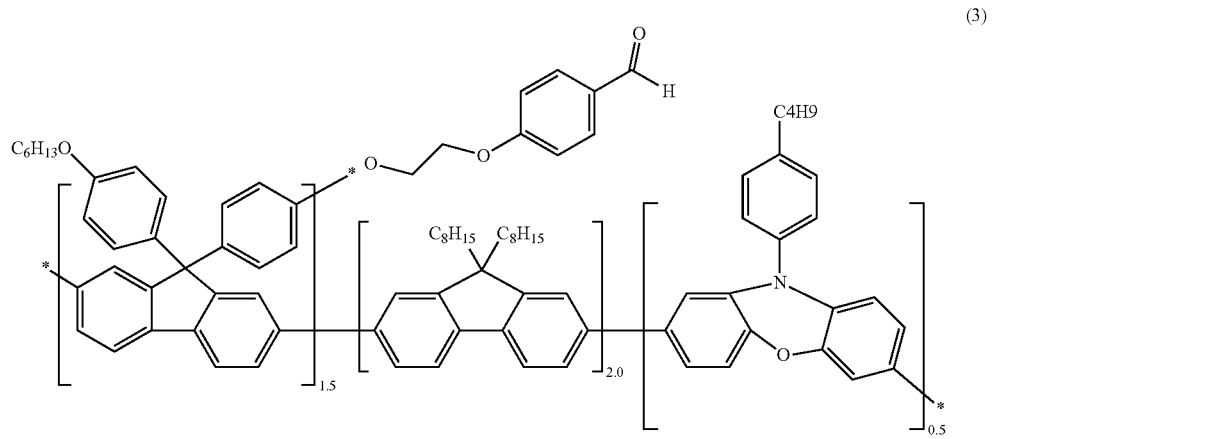

(3)

PFT demonstrated a very strong response magnitude to nonpolar vapors such as toluene, benzene, and others. FIG. 12 shows the results (variation in response frequency (line plot 72) and complex impedance (line plot 74)) of replicate exposures of the sensor to variable concentrations of toluene. Initial calculations of the detection limit of toluene (at S/N=3) resulted in a sub-ppm (0.9 ppm) detection limit Example 5

Quantitation of individual vapors in up to quaternary mixtures was achieved using a single resonant sensor. This outstanding result became possible from not only using a sensing film based on a ligand-protected metal nanoparticles film but also from applying specially developed data analysis algorithms of Ž(f) spectra or calculated parameters to perform vapor classification and quantitation. Quantitation of individual vapors in mixtures (FIG. 13) was performed with prediction errors <2% that were dependent on the types of vapors and the number of vapors in the mixture. Such capability of the developed sensors is critical for the selective multi-vapor detection.

Example 6

Quantitation of a two-vapor response pattern in the presence of variable number of interferences was achieved using a single resonant sensor. This quantitation was performed by rejecting the increasing number of interferences in the gas mixtures while performing quantitation and classification of analyte vapor mixtures (See FIG. 14). We constructed a pattern of concentrations of two model vapors (e.g., toluene and tetrahydrofuran) with their individual concentrations and as binary mixtures (See FIG. 14A). Using our previously developed ten-vapor generator system, this pattern of two vapors was mixed with an increasing number of interference vapors (See FIG. 14B). Diverse interference vapors (e.g., 1 to 8 interference vapors) such as water, acetonitrile, acetone, methyl salicylate, ethanol, 1-pentanol, 1-propanol, and salicylaldehyde were selected for testing at their concentrations of 0.05 P/Po. It was observed that individual analyte vapors (See FIG. 14C and FIG. 14D) were quantified well even in the presence of all eight interference vapors. In binary mixtures, tetrahydrofuran was also accurately quantified, while toluene quantitation was less accurate (See FIG. 14E), likely due to the smaller sensor signal. These results with model analyte and interference vapors provide the foundation for high selectivity sensing.

Example 7

Optimization of sensor excitation conditions was demonstrated to improve the orthogonality of the sensor response. This optimization was provided by the control of the mutual inductance between the wireless sensor and the pick-up coil of the sensor reader (network analyzer). The proper selection of the sensor excitation conditions gave the ability to discriminate between closely related analytes. FIG. 15A illustrates that under non-optimized conditions, vapor of heptane (he) of dielectric constant of 1.92 was not reliably discriminated from vapor of toluene (to) of dielectric constant of 2.38 as evidenced by the overlapping data points related to the sensor response to two types of vapors he and to. These vapors can be only discriminated from vapor of trichloroethylene (tr) of dielectric constant of 3.39. FIG. 15B illustrates that under optimized conditions, vapor of heptane (he) was reliably discriminated from vapor of toluene (to) and vapor of trichloroethylene (tr). This figure illustrates scores plots upon the principal components analysis (PCA) of multivariable response of an individual sensor coated with a ligand-protected metal nanoparticles film. "Blank" signifies exposure of the sensor to a carrier gas (nitrogen) and other data points (three data points per cluster) represent exposures of the sensor to four concentrations of vapors. The concentrations were 0.044, 0.089, 0.13, and 0.18 P/Po, wherein Po is the saturated vapor pressure of tested vapor and P is its partial pressure during the test.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A method for selective detection of at least two analytes with one wireless, multivariate, battery-free sensor, the method comprises the steps of:
    contacting at least two analytes with a sensor circuit, wherein the sensor circuit comprises at least one integrated circuit chip that is configured to accept inputs from at least two sensors, where the sensors are positioned in proximity to the chip or are integrated into the chip;
    detecting more than one analyte using at least two inputs into an integrated circuit chip of the sensor circuit where the inputs into the integrated circuit chip are from the same or from different sensing materials;

determining a multivariate response pattern of the sensor system upon sensor exposure to different analytes by performing a multivariate analysis of the response of at least two sensors; and identifying the analytes and concentrations of at least two analytes from this pattern, wherein one of the analytes is an analyte of interest to an end-user and the second analyte is an interference or another analyte of interest to the end-user.

2. The method of claim 1, wherein the sensor is a sensing node and is a part of the sensor network.

* * * * *